United States Patent
Chung

[19]

[11] Patent Number: 6,128,492
[45] Date of Patent: Oct. 3, 2000

[54] METHOD FOR TRACING CENTRALIZED PROCESS POSITION OF MOBILE STATION USING RADIO LAN

[75] Inventor: Hee Chang Chung, Daejon-shi, Rep. of Korea

[73] Assignee: Electronics and Telecommunications Research Institute, Daejon-shi, Rep. of Korea

[21] Appl. No.: 09/141,244

[22] Filed: Aug. 27, 1998

[30] Foreign Application Priority Data

Dec. 6, 1997 [KR] Rep. of Korea ............ 97-66545

[51] Int. Cl.[7] ................................ H04Q 7/20
[52] U.S. Cl. ......................... 455/435; 455/456
[58] Field of Search ..................... 455/432, 435, 455/456, 457, 502, 404; 340/573.1, 502; 128/202.22, 903; 370/338

[56] References Cited

U.S. PATENT DOCUMENTS

| | | | |
|---|---|---|---|
| 5,003,984 | 4/1991 | Muraki et al. ............... | 128/710 |
| 5,319,355 | 6/1994 | Russek ....................... | 340/573 |
| 5,626,630 | 5/1997 | Markowitz et al. ......... | 607/60 |
| 6,061,563 | 5/2000 | Lee ............................ | 455/435 |

OTHER PUBLICATIONS

Marc Chelouche et al., Digital Wireless Broadband Corporate and Private Networks: RNET Concepts and Applications, 1997, pp. 42–51.
Chai–Keong Toh, "Associativity–Based Routing for Ad–Hoc Mobile Networks", 1997, pp. 103–139.
Ad Kamerman, "Wireless LANs Untether Portable Control Systems", Oct. 1996, pp. 59–62.

*Primary Examiner*—Nguyen Vo
*Attorney, Agent, or Firm*—Cohen, Pontani, Lieberman & Pavane

[57] ABSTRACT

A centralized process position trace method of mobile station using radio LAN is provided, in which a position of a mobile station is traced in a building in order to transmit and receive data between mobile station and access point. A two-way communication method is provided in accordance with the invention, in which a position of a mobile station is traced in a building in order to transmit and receive data between mobile station and access point and a patient's emergent situation is informed from the mobile station to home position access point and vice versa by realizing the Medical Application Radio System (called MARS below) protocol suggested by IEEE802.11 in Medical Application Radio System.

1 Claim, 2 Drawing Sheets

METHOD FOR TRACING CENTRALIZED PROCESS POSITION OF MOBILE STATION USING RADIO LAN

BACKGROUND OF THE INVENTION

1. Field of the Invention

The present invention relates to a two-way communication method in which data can be transmitted and received between a transmitter attached to a moving patient and a central monitor receiver, more particularly, relates to a two-way application protocol algorithm in which, a position of a mobile Station (STA) is traced in a building in order to transmit and receive data between mobile station and Access Point (AP), whether a patient is in an emergent situation is determined and the emergency signal is transmitted to the mobile station attached to patient, by realizing the Medical Application Radio System (called MARS below) protocol suggested by IEEE802.11 in Medical Application Radio System (called MARS below).

2. Description of the Related Art

The MARS has a function in which some medical informations occurred in a monitoring sensor of moving patient are transmitted to an office where medical doctors or nurses reside and collected data are analyzed and processed. This system consists of home position access point installed in an office, transit access point installed in a corridor or a sick room and station point.

The MARS consists of a radio LAN and wire networks, and can construct communication network using public communication network or wire LAN. The wire network provides logical service function which is necessary for communicating between networks without any period interrupting destination address management and service, and can be consisted of conventional wire LAN communication network or public communication network.

Radio LAN consists of mobile station and access point which operate in 2.400 to 2.4835 GHz (83.5 MHz) of non-license band, and the access point has a radio access function and wire LAN communication network access function being distribution system. This system can transmit and receive informations bidirectionally through mobile station, access point and wire network.

UHF telemetry systems of conventional art (400 MHz) are one-way communication system, which consist of a transmitter attached to a patient and central monitor receiver and transmit information signals about patient's situation to central monitor receiver. The system has data transmission speed of 9.6 Kbps and has dedicated network. Its operating frequency is divided every 25 KHz in the band of 406 to 512 MHz.

SUMMARY OF THE INVENTION

An object of the invention is to provide a two-way communication method, in which a position of a mobile station is traced in a building in order to transmit and receive data between mobile station and access point and a patient's emergent situation is informed from the mobile station to home position access point and vice versa by realizing the Medical Application Radio System (called MARS below) protocol suggested by IEEE802.11 in Medical Application Radio System.

A method for tracing centralized process position of mobile station using radio LAN comprises the steps of completing the initialization procedure by inputting informations concerning with patient into a home position access point and a mobile station and registering them; requesting the mobile station to be associated with the home position access point after initializing the mobile station; confirming if the mobile station is registered, sending association confirmation signal when the mobile station is registered and requesting medical doctors or nurses to register the mobile station when the mobile station is not registered; checking periodically if the mobile station received beacon signal of the access point after receiving the association confirmation signal from the home position registration device (the first checking step); checking if the basic service network identifier is identified by checking and adjusting the access point identifier and basic service network identifier in the case that the mobile station received the beacon signal as a result of the first checking step (the second checking step); adjusting the synchronous clock in the case that the basic service network identifier is identified as a result of the second checking step; requesting the trunk access point to reassociate in the case that the basic service network identifier is not identified as a result of the second checking step, and checking if confirmation response for the reassociation from the trunk access point was received (the third checking step); adjusting the synchronous clock in the case that the confirmation response is received from the trunk access point as a result of the third checking step, and if not, informing the network of this and performing maintenance; checking the synchronous clock and adjusting if necessary in the case that the basic service network identifier is identified as a result of the second checking step; and adjusting the radio channel and clock and checking repeatedly if beacon signal is received in the case that the beacon informations of access point were not received, and then moving the first checking step if the beacon informations were received, and if not, checking the situation of mobile station in the maintenance procedure.

BRIEF DESCRIPTION OF THE DRAWINGS

The above object, and other features and advantages of the present invention will become more apparent by describing the preferred embodiment thereof with reference to the accompanying drawings, in which.

Similar reference characters refer to similar parts in the several views of the drawings.

DESCRIPTION OF THE PREFERRED EMBODIMENT

Medical Application Radio System (MARS) operates in the frequency of 2.400 to 2.4835 GHz (83.5 MHz) which are non-license band, adopts Gausian Frequency Shift Keying (GSFK) modulation method using frequency jump expansion band and constructs total 79 channels using 1 MHz channel band.

MARS consists of a mobile station and an access point, and the access point has a radio access function and wire LAN communication network function being a distribution system.

The access point and the mobile station consist of a radio part, a control processor and an Input Output Service Part (called IOSP). The access point consists of parallel port of personal computer and IOSP, and is connected to wire network through communication interface of personal computer.

Figure 1:
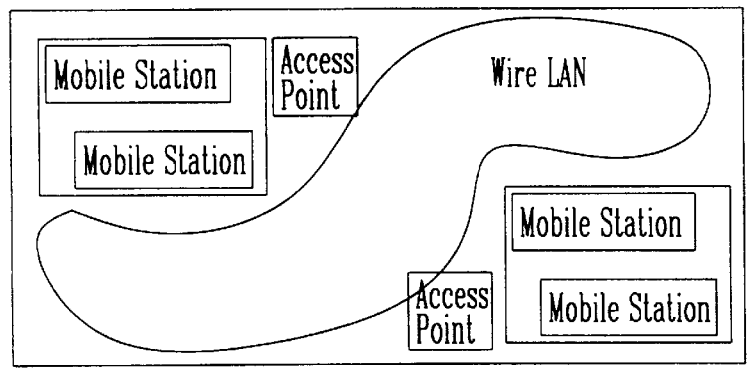
FIG. 1 is a hardware block diagram showing Medical Application Radio System (MARS) according to the invention.
Figure 2:
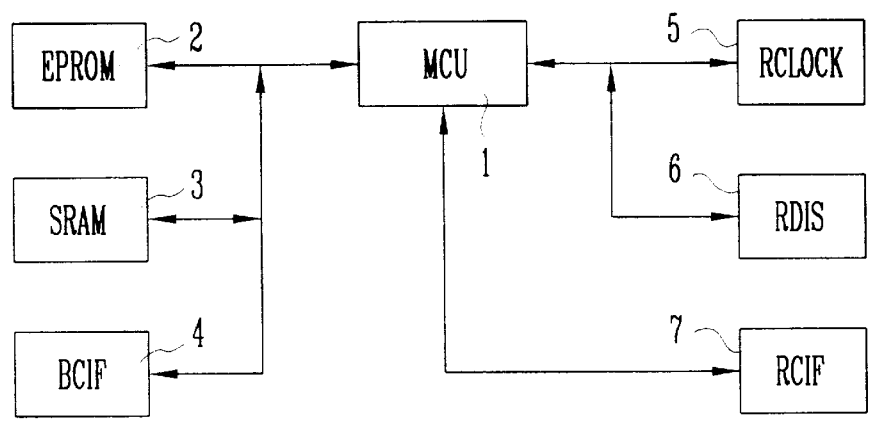
FIG. 2 is a structural diagram showing Input Output Service Part (IOSP) of Medical Application Radio System according to the invention.

FIG. 2 shows a structural block diagram of IOSP, in which IOSP is connected to the control system through serial and parallel port in the access point, and electrocardiograph and somatological signal monitoring system attached to a patient and a liquid crystal display and a speaker for displaying the transmitted and received signals in the mobile station.

IOSP consists of 8 bit microprocessor 1,128 byte EPROM 2,32 K byte RAM 3 and radio part, and performs position trace protocol function.

Board Control Interface (called BCIF below) 4 performs board reset, RS-232C serial port operation.

RCLOCK 5 supplies master clock. Radio Display (called RDSI below) consists of LCD control circuit and LCD and displays informations about systems or other relevant informations.

Radio Control interface (called RCIF below) 7 is connected to the 2.5 GHz frequency jump radio transmission apparatus through IOSP and transmits and receives control informations and packet data using 25 pins flat cable connector.

The control processor consists of 8 bit microprocessor, 32 K byte RAM, 128 K byte EPROM, radio part and peripheral device, and performs protocol function. The protocol consists of physical Layer, MAC Layer and application Layer.

Figure 3:
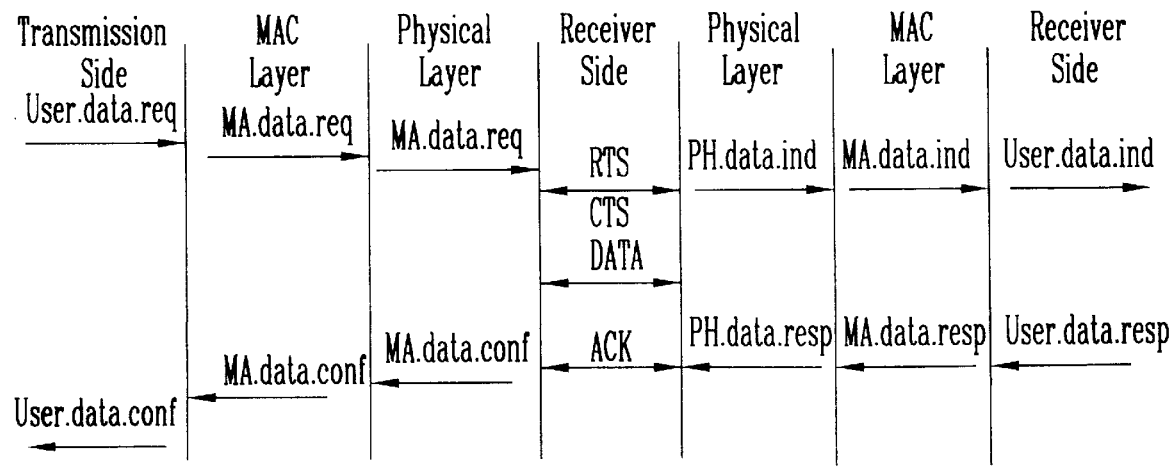
FIG. 3 shows a diagram of protocol setting for transmitting informations.

FIG. 3 shows a diagram of protocol setting for transmitting informations.

When some problems are found in the user function key or patient's sensor device in the application Layer, or in the centralized process access point, a data transmission request (Data_Req) primitive is transferred to the MAC Layer of station.

When the data transmission request (Data_Req) primitive is come down from higher Layer, the transmission site of MAC hierarchy constructs the frame in order to match the information structure of MAC Protocol Data Unit (MPDU) and transmits MAC data transmission request (MA. data_Req) primitive to the physical Layer.

According to Carrier Sense Multi Access/Collision Avoidance (CSMA/CA) procedure, if the transmission site receives Request To Send (RTS) packet—Clear To Send (CTS)—DATA—ACKnowledge (ACK) packet, the transmission site acknowledges the completion of transmission, and the physical Layer changes the MAC data transmission request (MA. data_Req) primitive to physical Layer data identification (PH_data_ind) primitive and transmits it to the receiver site.

Also, the receiver site sends down the data receiving response (Data_resp) primitive to the MAC Layer. After receiving the data receiving response (Data_resp) primitive, the receiver site MAC Layer completes the information transmission by sending down the data receiving response (Data_resp) primitive to the physical Layer and informing data response conformation (Data_conf) primitive to user Application Layer.

Figure 4:
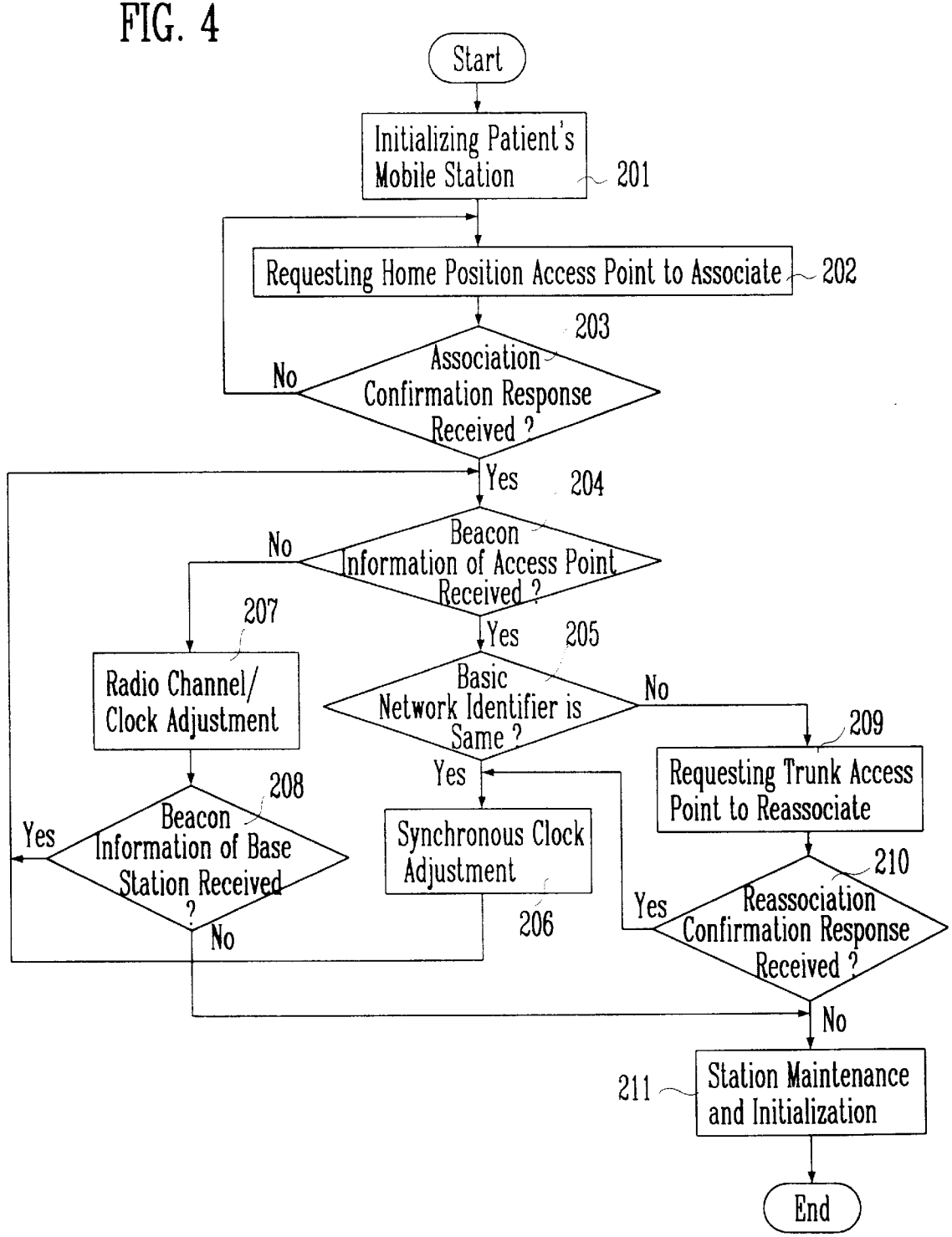
FIG. 4 is a flow chart which explains the method of using radio LAN according to the invention.

FIG. 4 is a flow chart which explains the method of using radio LAN according to the invention. The method for tracing position of mobile station is as follows. If the mobile station does not receive beacon messages which have time informations and its address broadcasted periodically from the access point, a channel scan operation starts in order to find adjacent access point. Network manager records informations concerned with mobile station in the program management table and operates the mobile station. The mobile station is registered in the home position access point at the time of initial installation by the association command, and uses reassociation command to register the mobile station in another access point before association.

The mobile station should be associated to the access point before transmitting data messages through an access point. The informations are provided between the mobile station and the access point using the association service, and the relevant informations for message exchange can be used through wire network. The mobile station is associated with an access point, and should respond necessarily when the access point requests some informations through wire network. The access point can be associated with several mobile station, and the communication can be obtained between the access point and the mobile station.

Reassociation is used to register the mobile station from one access point to another access point in the network. The reassociation service is a function which supports network mobility, that is, the mobile station moves and reassociates with other network in the Extended Service Set (ESS). The reassociation has a property that the association informations, that is, timer synchronism information and jump information can be changed during the mobile station is connected to same access point. The reassociation begins to operate by moving mobile station, and the mobile station can transmit and receive message to/from home position access point when the access point informs the home position access point of some informations about new mobile station.

Disassociation means that the registration of mobile station associated already is cancelled and it is impossible to communicate any more. This means that the cancel of information registered already is informed to all access points through wire network and no message is transmitted to disconnected mobile station. The disassociation service is requested by the connected mobile station or access point, and the disassociation service can not rejected from the connected one which is not request.

Also, when the access point is removed in the network or service, the mobile station is disassociated. The mobile station is also suggested to disassociate when it leaves the network.

MAC protocol always protects itself since the management hierarchy always monitors the mobile station regardless of the fact that mobile station requests disassociation service.

Receiver site processes RTS and CTS messages according to CSMA/CA procedure and then transmits management identification (MA.mgnt.ind), and the access point in receiver site informs home position access point of the relevant informations about the mobile station registered newly through wire network. The home position access point finds the position of mobile station through reassociated access point, and the reassociation is completed by requesting the disassociation of mobile station to the access point reassociated already.

The method for tracing centralized process mobile in accordance with the invention is explained using the flow chart.

First, informations concerning with patient are input and registered in home access point and mobile station, and then the initialization is completed (step 201). The mobile station requests the home position access point to associate after being initialized (step 202). The home position access point confirms if the mobile station is registered, and sends association confirmation signal when the mobile station is registered (step 203). If the mobile station is not registered, that is, not permitted to use, it needs to be registered by medical doctors or nurses. After receiving association confirmation, the mobile station checks if beacon signal of access point was received periodically (step 204).

If the mobile station receives beacon signal as a result of checking of step (204), the access point identifier and basic service network identifier are checked and adjusted, and it is identified if the basic service network identifier is identified (step 205). If the basic service network identifier is identified, the synchronous clock is adjusted (step 206) and the step returns to step (step 204).

If the basic service network identifier is not identified, the reassociation is requested to the trunk access point, and it is checked 5 times if the confirmation response for the reassociation from the trunk access point is received (step 210). If the confirmation response is received, the synchronous clock is adjusted (step 206), and if the confirmation response is not received, this situation is informed to network and maintenance is performed (step 211).

If the basic service network identifier is identified as a result of checking of step 205, it is the case that the mobile station is associated with same access point, and the synchronism clock is compared and adjusted if necessary (step 206).

When the beacon informations of the access point a re not received as a result of checking of step (step 204), radio channel and clock are adjusted (step 207) and it is checked repeatedly to the maximum, 5 times if the beacon informations of base station are received (step 208). If it is received, the step returns to step 204, if not, the step goes to step 211 of maintenance and the situation of mobile station is checked.

According to the invention, a two-way communication method is provided, in which a position of a mobile station is traced in a building in order to transmit and receive data between mobile station and access point and a patient's emergent situation is informed from the mobile station to home position access point and vice versa by realizing the Medical Application Radio System protocol suggested by IEEE802.11 in Medical Application Radio System.

While the present invention has been described and illustrated herein with reference to the preferred embodiment thereof it will be understood by those skilled in the art that various changes in form and details may be made therein without departing from the spirit and scope of the invention.

What is claimed is:

1. A method for tracing a centralized process position of a mobile station using a radio LAN, comprising the steps of:

completing an initialization procedure by inputting information concerning a patient into a home position access point and a mobile station and registering the information;

requesting the mobile station to be associated with the home position access point after initializing the mobile station;

confirming if the mobile station is registered, sending an association confirmation signal when the mobile station is registered and requesting medical doctors or nurses to register the mobile station when the mobile station is not registered;

in a first checking step checking periodically if the mobile station received a beacon signal of the access point after receiving an association confirmation signal from a home position registration device;

in a second checking step checking if a basic service network identifier is identified by checking and adjusting an access point identifier and basic service network identifier when the mobile station received a beacon signal as a result of the first checking step;

adjusting a synchronous clock when the basic service network identifier is identified as a result of the second checking step;

in a third checking step requesting a trunk access point to reassociate when the basic service network identifier is not identified as a result of the second checking step, and checking if confirmation response for the reassociation from the trunk access point was received;

adjusting the synchronous clock when the confirmation response is received from the trunk access point as a result of the third checking step, and if not, informing the network of this and performing maintenance;

checking the synchronous clock and adjusting if necessary when the basic service network identifier is identified as a result of the second checking step; and adjusting a radio channel and clock and checking repeatedly if the beacon signal is received when beacon information of the access point is not received, and then performing the first checking step if the beacon information was received, and if not, checking the mobile station in the maintenance procedure.

* * * * *